US009955895B2

(12) United States Patent
Jin et al.

(10) Patent No.: US 9,955,895 B2
(45) Date of Patent: May 1, 2018

(54) WEARABLE HEAD-MOUNTED, GLASS-STYLE COMPUTING DEVICES WITH EOG ACQUISITION AND ANALYSIS FOR HUMAN-COMPUTER INTERFACES

(71) Applicant: The Research Foundation for The State University of New York, Binghamton, NY (US)

(72) Inventors: Zhanpeng Jin, Vestal, NY (US); Sarah Laszlo, Binghamton, NY (US)

(73) Assignee: The Research Foundation for the State University of New York, Binghamton, NY (US)

( * ) Notice: Subject to any disclaimer, the term of this patent is extended or adjusted under 35 U.S.C. 154(b) by 759 days.

(21) Appl. No.: 14/533,617

(22) Filed: Nov. 5, 2014

(65) Prior Publication Data
US 2015/0126845 A1    May 7, 2015

Related U.S. Application Data

(60) Provisional application No. 61/900,397, filed on Nov. 5, 2013.

(51) Int. Cl.
| | | |
|---|---|---|
| A61B 5/04 | (2006.01) |
| A61B 5/0496 | (2006.01) |
| A61B 5/00 | (2006.01) |
| G06F 1/16 | (2006.01) |
| G06F 3/01 | (2006.01) |
| A61B 5/0488 | (2006.01) |
| G02B 27/01 | (2006.01) |

(52) U.S. Cl.
CPC .......... *A61B 5/0496* (2013.01); *A61B 5/6803* (2013.01); *A61B 5/726* (2013.01); *G02B 27/017* (2013.01); *G06F 1/163* (2013.01); *G06F 3/013* (2013.01); *G06F 3/015* (2013.01); *A61B 5/0488* (2013.01); *G02B 2027/014* (2013.01); *G02B 2027/0178* (2013.01); *G02B 2027/0187* (2013.01)

(58) Field of Classification Search
CPC ... A61B 5/0488; A61B 5/0496; A61B 5/6803; A61B 5/726; G02B 2027/014; G02B 2027/0178; G02B 2027/0187; G02B 27/017; G06F 1/163; G06F 3/013; G06F 3/015
See application file for complete search history.

(56) References Cited

PUBLICATIONS

English, Erik, et al. "EyePhone: A mobile EOG-based Human-Computer Interface for assistive healthcare." Neural Engineering (NER), 2013 6th International IEEE/EMBS Conference on. IEEE, 2013.

(Continued)

*Primary Examiner* — George Manuel
(74) *Attorney, Agent, or Firm* — Steven M. Hoffberg; Tully Rinckey PLLC

(57) ABSTRACT

A apparatus for detecting electrooculograph (EOG) signals, comprising: a pair of temple pieces connected to a bridging structure; at least one electrode on each temple piece configured to contact the skin at the temple, and to receive an EOG signal from a proximate orbital socket; a reference electrode displaced from each temple; and a processor configured to process signals from the sensors to detect saccade movements of the eyes. A wavelet-based algorithm permits analysis and coding of the saccade movements.

20 Claims, 8 Drawing Sheets

(56) References Cited

PUBLICATIONS

R. Barea, L. Boquete, M. Mazo, and E. Lopez. System for assisted mobility using eye movements based on EOG. IEEE Trans. Neural Syst. Rehabil. Eng., 10(4):209{218, Dec. 2002.
L. Bi, et al. EEG-based brain-controlled mobile robots: a survey. IEEE Trans. Human-Mach. Syst., 43(2):161{176, 2013.
Y. Chen and W. S. Newman. A human-robot interface based on electrooculography. In Proc. ICRA, pp. 243{248, 2004.
Q. Ding, K. Tong, and G. Li. Development of an EOG based human-computer interface. In Proc. EMBC, pp. 6829{6831, 2005.
Z. Jin, Y. Sun, and A. Cheng. Predicting cardiovascular disease from real-time ECG monitoring. In EMBC, pp. 6889{6892, 2009.
Q. X. Nguye and S. Jo. Electric wheelchair control using head pose free eye-gaze tracker. Electron. Lett., 48(13):750{752, Jun. 2012.
J. Oresko, Z. Jin, J. Cheng, S. Huang, Y. Sun, H. Duschl, and A. Cheng. A wearable smartphone-based platform for real-time cardiovascular disease detection via electrocardiogram processing. IEEE Trans. Info. Tech. Biomed., 14 (3):734{740, May 2010.
M. Tinati and B. Mozaffary. A wavelet packets approach to ECG baseline drift cancellation. Int'l J. Biomed. Imag., 2006:1-9, 2006.
X. Wang, et al. Leveraging mobile cloud for telemedicine: a performance study in medical monitoring. In Proc. NEBEC, 2013.

WEARABLE HEAD-MOUNTED, GLASS-STYLE COMPUTING DEVICES WITH EOG ACQUISITION AND ANALYSIS FOR HUMAN-COMPUTER INTERFACES

CROSS REFERENCE TO RELATED APPLICATION

The present application is a non-provisional of U.S. Provisional Patent Application No. 61/900,397, filed Nov. 5, 2013, the entirety of which is expressly incorporated herein by reference it its entirety.

FIELD OF THE INVENTION

The present invention relates to user inputs for the field of wearable virtual projection display devices.

BACKGROUND OF THE INVENTION

Human computer interaction (HCI) has gained widespread attention because it creates the possibility of users' interacting with computers and environments. Among all input pathways, electrooculography (EOG)-based systems [1-7] show great potential for controlling computers and devices by recognizing the user's eye movements, which is of particular significance to people with disabilities requiring hands-free alternatives (e.g., paralyzed or "locked-in" patients).

Electrooculography (EOG/E.O.G.) is a technique for estimating eye lateral based on changes in the inferred axis of the corneo-retinal dipole, with the retina having a negative potential. To measure eye movement, pairs of electrodes may be placed above and below or to the eye or to the left and right of the eye. The resting potential may vary based on illumination. Drift of the measured DC baseline potential and inferred axis of the eye. This can be compensated by periodic calibration, or analysis of the EOG signal for movements rather than position. Calibration can be achieved by simply having the user look forward, left and right, up and down, to set the center and range of the signal.

Some literature applies this label to analysis of electromyographic signals emitted by eye muscles. Note that the EMG signals reveal the activation of the muscle fiber action potentials, and are present as an alternating current signal whose amplitude and frequency spectrum characteristics may vary depending on eye movement, while the dipole measurement of the corneo-retinal dipole is a direct current measurement related to eye position.

Various efforts have been applied for implementing an EOG controlled human computer interface.

See (each of which is expressly incorporated herein by reference in their entirety):

[1] S. H. Kwon and H. C. Kim, "EOG-based glasses-type wireless mouse for the disabled," in Proceedings of the 21st Annual Int'l Conf. of the IEEE Engineering in Medicine and Biology Society (EMBC), pp. 592, 1999.

[2] A. Bulling, D. Roggen, and G. Troster, "It's in your eyes: towards context-awareness and mobile HCI using wearable EOG goggles," in Proceedings of 10th Int'l Conf. Ubiquitous Computing (UbiComp), pp. 84-93, 2008.

[3] A. Bulling, D. Roggen, and G. Troster, "Wearable EOG goggles: eye-based interaction in everyday environments," in Proceedings of CHI Extended Abstracts on Human Factors in Computing Systems (CHI EA), pp. 3259-3264, 2009.

[4] X. Zheng, X. Li, J. Liu, W. Chen, and Y. Hao, "A portable wireless eye movement controlled human-computer interface for the disabled," in Proceedings of Int'l Conf. on Complex Medical Engineering (ICME), pp. 1-5, 2009.

[5] X. Yong, M. Fatourechi, R. K. Ward, and G. E. Birch, "The design of a point-and-click system by integrating a self-paced brain-computer interface with an eye-tracker," IEEE Journal of Emerging and Selected Topics in Circuits and Systems, vol. 1, no. 4, pp. 590-602, 2011.

[6] A. Bulling, J. A. Ward, H. Gellersen, and G. Troster, "Eye movement analysis for activity recognition using electrooculography," IEEE Transactions on Pattern Analysis and Machine Intelligence, vol. 33, no. 4, pp. 741-753, 2011.

[7] Y. Hao, M. Controzzi, C. Cipriani, D. B. Popović, X. Yang, W. Chen, X. Zheng, and M. C. Carrozza, "Controlling hand-assistive devices: utilizing electrooculography as a substitute for vision," IEEE Robotics & Automation Magazine, vol. 20, no. 1, pp. 40-52, 2013.

[8] A. B. Usakli and S. Gurkan, "Design of a novel efficient human-computer interface: an electrooculagram based virtual keyboard," IEEE Trans. on Instrumentation and Measurement, vol. 59, no. 8, pp. 2099-2108, 2010.

[9] S. Wu, L. Liao, S. Lu, W. Jiang, S. Chen, and C. Lin, "Controlling a human-computer interface system with a novel classification method that uses electrooculography signals," IEEE Trans. on Biomedical Engineering, vol. 99, 2013.

[10] E. English, A. Hung E. Kesten, D. Latulipe, and Z. Jin, "EyePhone: A mobile EOG-based human-computer interface for assistive healthcare," in Proceedings of Int'l IEEE EMBS Conf. on Neural Engineering (NER), 2013.

Al-Haddad, A. A., R. Sudirman, and C. Omar. "Guiding Wheelchair Motion based on EOG Signals using Tangent Bug Algorithm." Computational Intelligence, Modelling and Simulation (CIMSiM), 2011 Third International Conference on. IEEE, 2011.

Barea, R., L. Boquete, M. Mazo, and E. Lopez. System for assisted mobility using eye movements based on EOG. IEEE Trans. Neural Syst. Rehabil. Eng., 10(4):209{218, December 2002.

Barea, Rafael, et al. "Sensory System for Implementing a Human-Computer Interface Based on Electrooculography." Sensors 11.1 (2010): 310-328.

Barea, Rafael, et al. "Wheelchair guidance strategies using EOG." Journal of intelligent and robotic systems 34.3 (2002): 279-299.

Bi, L., et al. EEG-based brain-controlled mobile robots: a survey. IEEE Trans. Human-Mach. Syst., 43(2):1611176, 2013.

Bulling, Andreas, Daniel Roggen, and Gerhard Tröster. "Wearable EOG goggles: Seamless sensing and context-awareness in everyday environments." Journal of Ambient Intelligence and Smart Environments 1.2 (2009): 157-171.

Calhoun, Gloria L., and Grant R. McMillan. "Hands-free input devices for wearable computers." Human Interaction with Complex Systems, 1998. Proceedings., Fourth Annual Symposium on. IEEE, 1998.

Chen, Y., and W. S. Newman. A human-robot interface based on electrooculography. In Proc. ICRA, pages 243{248, 2004.

Deng, Lawrence Y., et al. "EOG-based Human-Computer Interface system development." Expert Systems with Applications 37.4 (2010): 3337-3343.

Deng, Lawrence Y., et al. "EOG-based signal detection and verification for HCI." Machine Learning and Cybernetics, 2009 International Conference on. Vol. 6. IEEE, 2009.

Ding, Q., K. Tong, and G. Li. Development of an EOG based human-computer interface. In Proc. EMBC, pages 6829{6831, 2005.

Ding, Qiuping, Kaiyu Tong, and Guang Li. "Development of an EOG (electrooculography) based human-computer interface." Engineering in Medicine and Biology Society, 2005. IEEE-EMBS 2005. 27th Annual International Conference of the. IEEE, 2006.

Duchowski. A. T., Eye Tracking Methodology: Theory and Practice. Springer-Verlag, London, UK, 2007.

Estrany, B., et al. "Human computer interface by EOG tracking." Proceedings of the 1st international conference on PErvasive Technologies Related to Assistive Environments. ACM, 2008.

Jin, Z., Y. Sun, and A. Cheng. Predicting cardiovascular disease from real-time ECG monitoring. In EMBC, pages 6889{6892, 2009.

Joyce, Carrie A., et al. "Tracking eye fixations with electrooccular and electroencephalographic recordings." Psychophysiology 39.05 (2002): 607-618.

Kang, S-K., et al. "EOG and Marker Recognition for Wearable User Interface." TENCON 2007-2007 IEEE Region 10 Conference. IEEE, 2007.

Kanoh, Shin'ichiro, et al. "Method of Menu Selection by Gaze Movement Using AC EOG Signals." IEEJ Transactions on Electronics, Information and Systems 129 (2009): 1822-1827.

Kaufman, Arie E., Amit Bandopadhay, and Bernard D. Shaviv. "An eye tracking computer user interface." Virtual Reality, 1993. Proceedings., IEEE 1993 Symposium on Research Frontiers in. IEEE, 1993.

Kelly, Simon P., et al. "Visual spatial attention tracking using high-density SSVEP data for independent brain-computer communication." Neural Systems and Rehabilitation Engineering, IEEE Transactions on 13.2 (2005): 172-178.

Kirbis, M., and Iztok Kramberger. "Multi Channel EOG Signal Recognition for an Embedded Eye Movement Tracking Device." Systems, Signals and Image Processing, 2009. IWSSIP 2009. 16th International Conference on. IEEE, 2009.

Lin, Chern-Sheng, et al. "Powered wheelchair controlled by eye-tracking system." Optica Applicata 36.2/3 (2006): 401.

Merino, Manuel, et al. "A method of EOG signal processing to detect the direction of eye movements." Sensor Device Technologies and Applications (SENSORDEVICES), 2010 First International Conference on. IEEE, 2010.

Nguye, Q. X., and S. Jo. Electric wheelchair control using head pose free eye-gaze tracker. Electron. Lett., 48(13): 750{752, June 2012.

Oresko, J., Z. Jin, J. Cheng, S. Huang, Y. Sun, H. Duschl, and A. Cheng. A wearable smartphone-based platform for real-time cardiovascular disease detection via electrocardiogram processing. IEEE Trans. Info. Tech. Biomed., 14(3):734{740, May 2010.

Patmore, David W., and R. Benjamin Knapp. "Towards an EOG-based eye tracker for computer control." Proceedings of the third international ACM conference on Assistive technologies. ACM, 1998.

Schroeder, William E. "Head-mounted computer interface based on eye tracking." Visual Communications '93. International Society for Optics and Photonics, 1993.

Tinat, M., and B. Mozaffary. A wavelet packets approach to ECG baseline drift cancellation. Int'l J. Biomed. Imag., 2006:1-9, 2006.

Tsui, Chun Sing Louis, et al. "EMG-based hands-free wheelchair control with EOG attention shift detection." Robotics and Biomimetics, 2007. ROBIO 2007. IEEE International Conference on. IEEE, 2007.

Venkataramanan, S., et al. "Biomedical instrumentation based on electrooculogram (EOG) signal processing and application to a hospital alarm system." Intelligent Sensing and Information Processing, 2005. Proceedings of 2005 International Conference on. IEEE, 2005.

Vidal, Mélodie, Andreas Bulling, and Hans Gellersen. "Analysing EOG signal features for the discrimination of eye movements with wearable devices." Proceedings of the 1st international workshop on pervasive eye tracking & mobile eye-based interaction. ACM, 2011.

Wang, X. et al. Leveraging mobile cloud for telemedicine: a performance study in medical monitoring. In Proc. NEBEC, 2013.

Zhang, Lelin, et al. "Wireless physiological monitoring and ocular tracking: 3D calibration in a fully-immersive virtual health care environment." Engineering in Medicine and Biology Society (EMBC), 2010 Annual international conference of the IEEE. IEEE, 2010.

See also, US Patent Applications and Patent Nos. (each of which is expressly incorporated herein by reference in their entirety): 20140316230; 20140303428; 20140278475; 20140277739; 20140275849; 20140275829; 20140266787; 20140257540; 20140257055; 20140253303; 20140249853; 20140249760; 20140249600; 20140249429; 20140249379; 20140247155; 20140247154; 20140247151; 20140247150; 20140247149; 20140247147; 20140247146; 20140247144; 20140247137; 20140247136; 20140246917; 20140246502; 20140246501; 20140246500; 20140246499; 20140246498; 20140246497; 20140245791; 20140245790; 20140245789; 20140245788; 20140245787; 20140245786; 20140245785; 20140245784; 20140245783; 20140241216; 20140235965; 20140229302; 20140223462; 20140222101; 20140221850; 20140221849; 20140221791; 20140221790; 20140221789; 20140221785; 20140221784; 20140221780; 20140221779; 20140213937; 20140204029; 20140204025; 20140198936; 20140194769; 20140194768; 20140194702; 20140184496; 20140180502; 20140172310; 20140171749; 20140163425; 20140163409; 20140148723; 20140143064; 20140140567; 20140129259; 20140121476; 20140114205; 20140114165; 20140104059; 20140094707; 20140078049; 20140077946; 20140076318; 20140073880; 20140063055; 20140063054; 20140062682; 20140058528; 20140058218; 20140057232; 20140055284; 20140051944; 20140051943; 20140051942; 20140049627; 20140031711; 20130344465; 20130336528; 20130317576; 20130317415; 20130317384; 20130317382; 20130314303; 20130314243; 20130310907; 20130310676; 20130304165; 20130303837; 20130297218; 20130297217; 20130296987; 20130282339; 20130278631; 20130276785; 20130268019; 20130237867; 20130231574; 20130211291; 20130204114; 20130197322; 20130194177; 20130190556; 20130184787; 20130178718; 20130172759; 20130172691; 20130158368; 20130158367; 20130138010; 20130131755; 20130131464; 20130128118; 20130127980; 20130120246; 20130102928; 20130096442; 20130095459; 20130091515; 20130090931; 20130072807; 20130069780; 20130060097; 20130046181; 20130042010; 20130009783; 20120330109; 20120323087; 20120321759; 20120320336; 20120302842; 20120300061; 20120296569; 20120277820; 20120277618; 20120277548; 20120274593; 20120272179; 20120256833; 20120251989; 20120249797; 20120245474; 20120245464;

20120245439; 20120242698; 20120242697; 20120242678; 20120242501; 20120236031; 20120236030; 20120235900; 20120235887; 20120235886; 20120235885; 20120235884; 20120235883; 20120229248; 20120218301; 20120218172; 20120212499; 20120212484; 20120212414; 20120212406; 20120212400; 20120212399; 20120212398; 20120206485; 20120206335; 20120206334; 20120206323; 20120206322; 20120203725; 20120200601; 20120200499; 20120200488; 20120194553; 20120194552; 20120194551; 20120194550; 20120194549; 20120194420; 20120194419; 20120194418; 20120179061; 20120172682; 20120127426; 20120123232; 20120109399; 20120105324; 20120095357; 20120095352; 20120092157; 20120092156; 20120088987; 20120083668; 20120078448; 20120075168; 20120075124; 20120075123; 20120062445; 20120053508; 20120053472; 20120053395; 20120022365; 20120022340; 20120016431; 20110314530; 20110313760; 20110301488; 20110301487; 20110301441; 20110298706; 20110298702; 20110295142; 20110251985; 20110238685; 20110231757; 20110227820; 20110227813; 20110227812; 20110225536; 20110222745; 20110221897; 20110221896; 20110221793; 20110221672; 20110221671; 20110221670; 20110221669; 20110221668; 20110221659; 20110221658; 20110221657; 20110221656; 20110214082; 20110213664; 20110213211; 20110181422; 20110161163; 20110125046; 20110118619; 20110116046; 20110115624; 20110105859; 20110063073; 20110061647; 20110029044; 20110029038; 20110028799; 20110028798; 20110015503; 20110015469; 20100331630; 20100286532; 20100280372; 20100280338; 20100274321; 20100240982; 20100228145; 20100220904; 20100217100; 20100204614; 20100201621; 20100197996; 20100195770; 20100177968; 20100160808; 20100113898; 20100106044; 20100099954; 20100087701; 20100076333; 20100069780; 20100049008; 20100042011; 20100030101; 20100030092; 20100030089; 20100007512; 20090318779; 20090312998; 20090309747; 20090299209; 20090295738; 20090289895; 20090273562; 20090271122; 20090264789; 20090227877; 20090227876; 20090221928; 20090216091; 20090214118; 20090188502; 20090177702; 20090150821; 20090149778; 20090141007; 20090136098; 20090105785; 20090099474; 20090082831; 20090082829; 20090082639; 20080294019; 20080266257; 20080243017; 20080243014; 20080218472; 20080208072; 20080201278; 20080183090; 20080183082; 20080181452; 20080177193; 20080171943; 20080161707; 20080154111; 20080104415; 20080097235; 20080084539; 20080071326; 20080071150; 20080059138; 20080056611; 20080055248; 20080021340; 20080004904; 20080001735; 20070293915; 20070282566; 20070276439; 20070276270; 20070273504; 20070270706; 20070265533; 20070250345; 20070250134; 20070250121; 20070249952; 20070208269; 20070167858; 20070146368; 20070135727; 20070123758; 20070055115; 20070030246; 20070015976; 20070010748; 20060293608; 20060290663; 20060281980; 20060266356; 20060200035; 20060200034; 20060122529; 20060094466; 20060089541; 20060077064; 20060061544; 20050283039; 20050243054; 20050234518; 20050222643; 20050215847; 20050195165; 20050144042; 20050115561; 20050113703; 20050113650; 20050085744; 20050085738; 20050080348; 20050047629; 20050033122; 20040267152; 20040193068; 20040143170; 20040046777; 20030139783; 20030139683; 20030083596; 20030069516; 20030016207; 20020151771; 20020135618; 20020077534; 20020039111; U.S. Pat. Nos. 8,878,796; 8,878,782; 8,874,211; 8,870,766; 8,870,764; 8,862,307; 8,862,219; 8,852,098; 8,851,669; 8,842,071; 8,831,702; 8,830,164; 8,823,527; 8,821,495; 8,818,513; 8,818,498; 8,814,691; 8,812,098; 8,805,527; 8,805,513; 8,805,501; 8,805,489; 8,798,698; 8,793,620; 8,784,893; 8,784,322; 8,784,293; 8,777,958; 8,775,340; 8,768,482; 8,768,449; 8,764,651; 8,762,733; 8,762,202; 8,761,890; 8,758,018; 8,757,163; 8,750,971; 8,747,336; 8,747,313; 8,744,587; 8,733,290; 8,727,978; 8,725,244; 8,721,341; 8,717,292; 8,715,033; 8,711,462; 8,708,904; 8,708,903; 8,708,884; 8,706,205; 8,706,182; 8,692,677; 8,684,926; 8,684,922; 8,684,900; 8,680,991; 8,663,106; 8,655,437; 8,655,428; 8,652,038; 8,647,268; 8,641,612; 8,639,322; 8,639,313; 8,635,105; 8,628,462; 8,626,301; 8,626,282; 8,626,259; 8,617,068; 8,616,208; 8,615,283; 8,614,676; 8,602,555; 8,591,430; 8,573,980; 8,570,176; 8,569,277; 8,562,527; 8,560,072; 8,556,951; 8,548,852; 8,540,369; 8,538,514; 8,533,042; 8,532,786; 8,531,291; 8,525,788; 8,525,687; 8,525,673; 8,523,758; 8,522,779; 8,515,529; 8,512,221; 8,509,884; 8,509,882; 8,500,636; 8,494,905; 8,494,610; 8,493,390; 8,488,246; 8,484,081; 8,482,859; 8,478,486; 8,477,425; 8,475,368; 8,473,345; 8,473,045; 8,472,120; 8,467,133; 8,466,875; 8,464,288; 8,461,988; 8,460,322; 8,457,746; 8,449,471; 8,449,116; 8,442,640; 8,442,638; 8,437,843; 8,434,868; 8,428,741; 8,425,415; 8,419,654; 8,405,610; 8,401,651; 8,400,313; 8,398,546; 8,396,744; 8,392,255; 8,392,254; 8,392,253; 8,392,251; 8,392,250; 8,386,313; 8,386,312; 8,386,244; 8,382,484; 8,380,314; 8,376,965; 8,374,701; 8,371,307; 8,369,940; 8,369,936; 8,368,641; 8,357,101; 8,355,769; 8,352,012; 8,346,354; 8,345,191; 8,344,911; 8,340,981; 8,335,716; 8,335,715; 8,332,038; 8,328,718; 8,323,204; 8,323,189; 8,323,188; 8,321,023; 8,311,622; 8,308,661; 8,306,265; 8,301,232; 8,290,596; 8,285,389; 8,281,787; 8,280,503; 8,271,074; 8,270,814; 8,254,634; 8,244,340; 8,242,880; 8,226,569; 8,220,466; 8,218,825; 8,209,224; 8,203,530; 8,195,289; 8,162,846; 8,157,732; 8,157,731; 8,147,407; 8,131,373; 8,121,693; 8,121,673; 8,108,036; 8,104,470; 8,103,333; 8,096,946; 8,096,303; 8,080,014; 8,079,953; 8,073,534; 8,069,852; 8,068,904; 8,059,136; 8,055,348; 8,044,766; 8,036,750; 8,032,842; 8,021,299; 8,019,428; 8,013,837; 8,010,347; 8,002,553; 8,000,793; 7,997,266; 7,993,279; 7,992,567; 7,991,195; 7,975,700; 7,969,416; 7,967,439; 7,959,567; 7,945,865; 7,934,506; 7,925,354; 7,917,222; 7,896,807; 7,894,890; 7,885,700; 7,869,881; 7,865,235; 7,860,455; 7,848,795; 7,835,581; 7,830,249; 7,805,196; 7,803,119; 7,803,118; 7,797,050; 7,797,040; 7,794,406; 7,787,946; 7,785,257; 7,783,353; 7,774,052; 7,766,827; 7,764,283; 7,755,602; 7,751,878; 7,749,154; 7,747,323; 7,739,126; 7,733,224; 7,727,139; 7,715,894; 7,706,992; 7,706,884; 7,702,502; 7,684,856; 7,674,230; 7,672,728; 7,654,948; 7,647,114; 7,643,875; 7,640,055; 7,639,146; 7,606,392; 7,596,413; 7,591,265; 7,583,819; 7,575,005; 7,572,225; 7,559,903; 7,558,622; 7,554,549; 7,539,533; 7,539,532; 7,522,344; 7,515,054; 7,509,166; 7,502,643; 7,502,498; 7,488,294; 7,486,991; 7,486,986; 7,469,697; 7,468,040; 7,460,906; 7,454,313; 7,420,472; 7,396,331; 7,376,459; 7,363,076; 7,351,524; 7,346,391; 7,297,119; 7,285,090; 7,269,455; 7,266,413; 7,260,436; 7,231,245; 7,204,250; 7,194,313; 7,177,678; 7,167,743; 7,117,108; 7,108,982; 7,070,571; 7,035,685; 7,024,234; 7,020,508; 7,013,258; 6,964,023; 6,928,354; 6,920,358; 6,875,174; 6,842,670; 6,811,538; 6,777,195; 6,740,032; 6,720,984; 6,697,930; 6,665,560; 6,636,763; 6,625,485; 6,595,929; 6,587,725; 6,575,902; 6,560,486; 6,553,252; 6,530,884; 6,511,424; 6,496,724; 6,491,647; 6,428,490; 6,425,861; 6,424,333; 6,419,629; 6,416,480; 6,398,721; 6,397,845; 6,377,833; 6,375,614; 6,370,414; 6,325,475; 6,306,088; 6,275,213; 6,259,889; 6,246,382; 6,231,187; 6,204,828; 6,175,762; 6,171,258; 6,152,563; 6,148,280; 6,097,927; 6,094,182; 6,092,058; 6,091,334; 6,088,017; 6,070,098; 6,050,962; 6,050,940; 6,033,073; 6,032,072; 5,999,846; 5,933,210; 5,930,

741; 5,851,193; 5,826,579; 5,823,190; 5,813,993; 5,762,611; 5,751,260; 5,728,680; 5,726,916; 5,724,987; 5,701,894; 5,694,939; 5,689,619; 5,687,291; 5,649,061; 5,645,068; 5,644,324; 5,622,168; 5,592,401; 5,570,698; 5,517,021; 5,513,649; 5,491,492; 5,467,777; 5,447,166; 5,422,689; 5,363,858; 5,360,971; 5,331,959; 5,299,118; 5,293,187; 5,259,390; 5,204,703; 5,137,027; 5,047,930; 4,973,149; 4,950,069; 4,889,422; 4,838,681; 4,836,670; 4,817,633; 4,653,001; 4,570,637; 4,561,448; 4,474,186; 4,417,592; 4,320,768; 4,109,648; 4,105,302; and 3,969,020.

SUMMARY OF THE INVENTION

The present technology explores a synergistic solution to transform emerging wearable virtual projection display devices, e.g., Google Glass, into an eye-controlled mobile human-computer interaction device, which can be seamlessly extended to a hands-free assistive control system for people with disabilities or special needs. The technology detects and removes artifacts from EOG signals, recognizing and distinguishing various types and levels of eye movements. The EOG signals may be used to provide a comprehensive eye movement encoding language for eye-controlled HCI applications.

However, acquiring clean EOG from a wearable device is difficult, due to bulkiness and inconvenient configurations of existing EOG acquisition devices that may easily loosen electrode connections (FIGS. 1 and 2). To address this obstacle, a human computer interface (HCI) paradigm taking advantage of the recently emerging wearable head-mounted, glass-style computing devices (e.g., Google Glass, FIG. 3). Specifically, the design embeds a pair of small electrodes placed inside the arms of an eyeglass frame (arranged as in FIGS. 5A and 5B). These electrodes record the electrooculography (EOG; [8,9]) signals in the horizontal direction, and enable users to control the HCI, wirelessly tethered mobile devices, or any other wireless connected devices via intentional eye movements. The technology ensures both reliable EOG signals acquisition and comfortable user experience.

Vertical EOG tracking is not directly supported, though instead of a single electrode on each temple arm, a pair of electrodes displaced vertically may be provided at the temple, to yield some vertical information. This has the added advantage that the pair of electrodes may be processed together for horizontal tracking to reduce some noise sources, such as EMG signals.

The movement of the eyes contains a rich source of information and has been widely used as a tool to investigate visual cognition. Existing eye trackers are usually developed using video-based systems [1, 8], which are expensive and also require image processing tasks with bulky auxiliary equipment. Eye movement characteristics such as saccades, fixations, and blinks, have already been investigated for hands-free operation of static human-computer interfaces [3, 4]. However, these existing studies only focused on exploring the links between the tasks and eye movements; little research has been done to use eye movement as a more basic source of information in the HCI system. Under the Google Glass-based mobile HCI paradigm, the eye movements are examined for use in a wide variety of controlling interactions with wearable computing devices, according to a language encoding framework.

Several algorithmic contributions are provided to address the following technical challenges:

(1) removal and compensation of artifacts and noise in EOG signals, (2) detection of intentional eye-movement events, and (3) recognition and encoding of more complex eye gestures consisting of a series of distinct eye movements.

Moreover, the present approach provides an effective and user-friendly means for people with disabilities or special needs to achieve true "hands-free" control interfaces.

Eye movements contain resourceful information that may be mapped to control instructions in HCI systems. The limited recognition accuracy and resolution in conventional vision-based eye movement trackers make them less effective in distinguishing finer eye movement amplitudes. In the present technology, the EOG signals can be continuously and accurately measured by the electrodes inside the eyeglass frame arms, which enables the detection of finer eye movements (FIG. 6). Thus eye movements are encoded by mapping saccades with different directions and amplitude to specific controlling instructions.

It is noted that, assuming the eyes move together, and that only the joint left-right horizontal movement signal is desired, then the two electrodes in the temple arms could provide a sufficient signal. However, a central electrode or electrodes may also be provided at the nose, for example using conductive silicone rubber nose-pads, which then separate the signals coming from each respective eye.

It is therefore an object to provide an apparatus for detecting electrooculograph (EOG) signals, comprising: a pair of temple pieces connected to a bridging structure; at least one electrode on each temple piece configured to contact the skin at the temple, and to receive an EOG signal from a proximate orbital socket; a reference electrode displaced from each temple; and a processor configured to process signals from the at least one electrode on each temple piece and the reference electrode to detect saccade movements of the eyes.

The at least one electrode on each temple piece may be configured to contact the skin at the temple comprises at least two electrodes, configured to determine changes in a vertical and horizontal axis of the EOG signal.

The processor may be configured to characterize an amplitude and a sign of an EOG signal.

The processor may be further configured to characterize a sequence of states of an EOG signal as a single user command selected from a wordbook of valid user commands.

The processor may be further configured to perform baseline drift compensation by performing a wavelet transform decomposition of the EOG signal to provide wavelet transform coefficients, estimate a baseline drift based on the wavelet transform coefficients, and to compensate the baseline drift based on the estimated baseline drift.

The processor may be further configured to: perform an approximated multilevel 1D wavelet decomposition at level nine using Daubechies wavelets on each EOG signal to produce a set of decomposition coefficients; estimating a drift of the EOG baseline using the decomposition coefficients; and subtracting the estimated drift of the EOG baseline from each EOG signal.

The processor may be further configured to implement median filter denoising, having a window sufficiently small to retain short signal pulses associated with eye blinks.

The processor may be configured to separately analyze movement of right and left eyes separately.

The processor may be configured to determine consistency of right and left eye saccadic movements.

The processor may be further configured to: perform a continuous wavelet transform (CWT) on the EOG signals; applying a threshold on the coefficients of the CWT transform to segment the EOG signal into periods of saccadic movement and fixation; filtering saccadic periods based on duration; and determining a signed saccade amplitude for each filtered period.

The processor may be further configured to:

perform a Continuous Wavelet Transform (CWT) on the EOG signals s, wherein the CWT first computes continuous 1D wavelet coefficients at scale 20 using a Haar mother wavelet, wherein: $\psi(t)$ is the mother wavelet;

$$C_b^a(s) = \int_R \frac{1}{\sqrt{a}} \psi\left(\frac{t-b}{a}\right) dt$$

are the wavelet coefficients $C_b^a$ of s at scale a and position b; applying a threshold $th_{sd}$ on the coefficients $C_i(s) = C_i^{20}(s)$, to create a vector M with elements $M_i$:

$$M_i = \begin{cases} 1, & \forall_i : C_i(s) < -th_{sd} \\ -1, & \forall_i : C_i(s) > th_{sd} \\ 0, & \forall_i : -th_{sd} \le C_i(s) \le th_{ed} \end{cases}$$

to divide the EOG signal into periods of saccadic (M=1,−1) and fixational (M=0) segments; removing saccadic segments shorter than 20 ms and longer than 200 ms; determining a saccade amplitude SA for each segment as a difference in EOG signal amplitude from a baseline EOG signal amplitude, and determining a saccade direction based on a sign of the corresponding elements in M.

An amplitude of an EOG signal during a saccade movement may be corrected for a change in baseline by subtracting an amplitude of an EOG signal during a time when a saccade is not detected temporally proximate to the saccade movement.

It is also an object to provide a method for detecting electrooculograph (EOG) signals, comprising: providing a pair of temple pieces connected to a bridging structure to a human or animal, having at least one electrode on each temple piece configured to contact the skin at the temple, and to receive an EOG signal from a proximate orbital socket and a reference electrode displaced from each temple; and processing electronic signals from the at least one electrode on each temple piece to detect saccade movements of the eyes.

The processing may further comprise determining a baseline EOG signal amplitude during an absence of saccade movements, and determining an amplitude and a sign of an EOG signal during a saccade movement.

The method may further comprise characterizing a sequence of a plurality of amplitudes and signs of an EOG signal over a period of time as a single user command selected from a wordbook of valid user commands.

The at least one electrode on each temple piece may be configured to contact the skin at the temple comprises a plurality of electrodes on each temple piece, configured to determine changes in a vertical and horizontal axis of the EOG signal.

The method may further comprise: compensating for a drift of the EOG baseline using decomposition coefficients of a wavelet decomposition on each EOG signal; and implementing a median filter to denoise the baseline corrected EOG signal, having a window sufficiently small to retain short signal pulses associated with eye blinks. The method may further still comprise determining, based on coefficients of a continuous wavelet transform of the EOG signals, respective periods of eye saccadic movement and eye fixation; filtering the periods of eye saccadic movement based on duration to eliminate periods of eye saccadic movement below and above respective lower and upper thresholds; and determining a signed saccade amplitude for each filtered period.

It is a still further object to provide a method for detecting electrooculograph (EOG) signals from eyes of a human or animal, comprising: providing a pair of temple pieces connected to a bridging structure supported by a nose of the human or animal, having at least one electrode on each temple piece configured to contact the skin at the temple, substantially without contacting an infraorbital facial surface, and to receive an EOG signal from a proximate orbital socket and a reference electrode displaced from each temple; processing electronic signals from the at least one electrode on each temple piece and the reference electrode to characterize an amplitude and direction of saccadic movements of the eyes and fixation of the eyes; and interpreting sequences comprising a plurality of characterized amplitudes and directions of saccadic movements of the eyes and fixations of the eyes as a user command.

The method may further comprise processing electronic signals from the at least one electrode on each temple piece and the reference electrode to characterize electromyographic signals.

The form factor of the system preferably takes the form of eyeglasses or half-rim (upper) frames, with electrode pads on the temple arms, which may be, for example, conductive carbon powder filled silicone rubber, which may be provided as a single pad, or a split pad, which further may be physically divided as multiple pads, or as a single structure with an insulating barrier. The pad is preferably located near the zygomatic arch. The reference electrode may be provided at the nose bridge, which would generally isolate left and right orbital sockets. The reference may also be provided at or behind the ear. Indeed, signals may be processed from all contact locations. The system may be powered by a primary battery, such as a hearing aid-type battery, a rechargeable battery, a solar cell (e.g., on the outside surface of the temple arm), or other known means. The technology may be embedded into a wearable computer system, such as Google Glass, or other electronic device that requires hand-free control, e.g., an MP3 type music player, GoPro® video camera, or the like. The system may also incorporate a microphone and/or other sensors, such as magnetometer/compass, accelerometer (e.g., 3 axis), anemometer, eye gaze direction sensor/video camera, gyroscope (e.g., 3 axis), inclinometer, GPS/aGPS, RF triangulation, etc., which may provide their traditional functions in addition to integrating to provide added or complementary functionality to the EOG sensor. Similarly, the EOG and sensors may be used for control of a human computer interface, or for other purposes, which may include medical diagnosis or monitoring.

These and other objects will become apparent from a review of the embodiments described below.

DETAILED DESCRIPTION OF THE PREFERRED EMBODIMENTS

Figure 4:
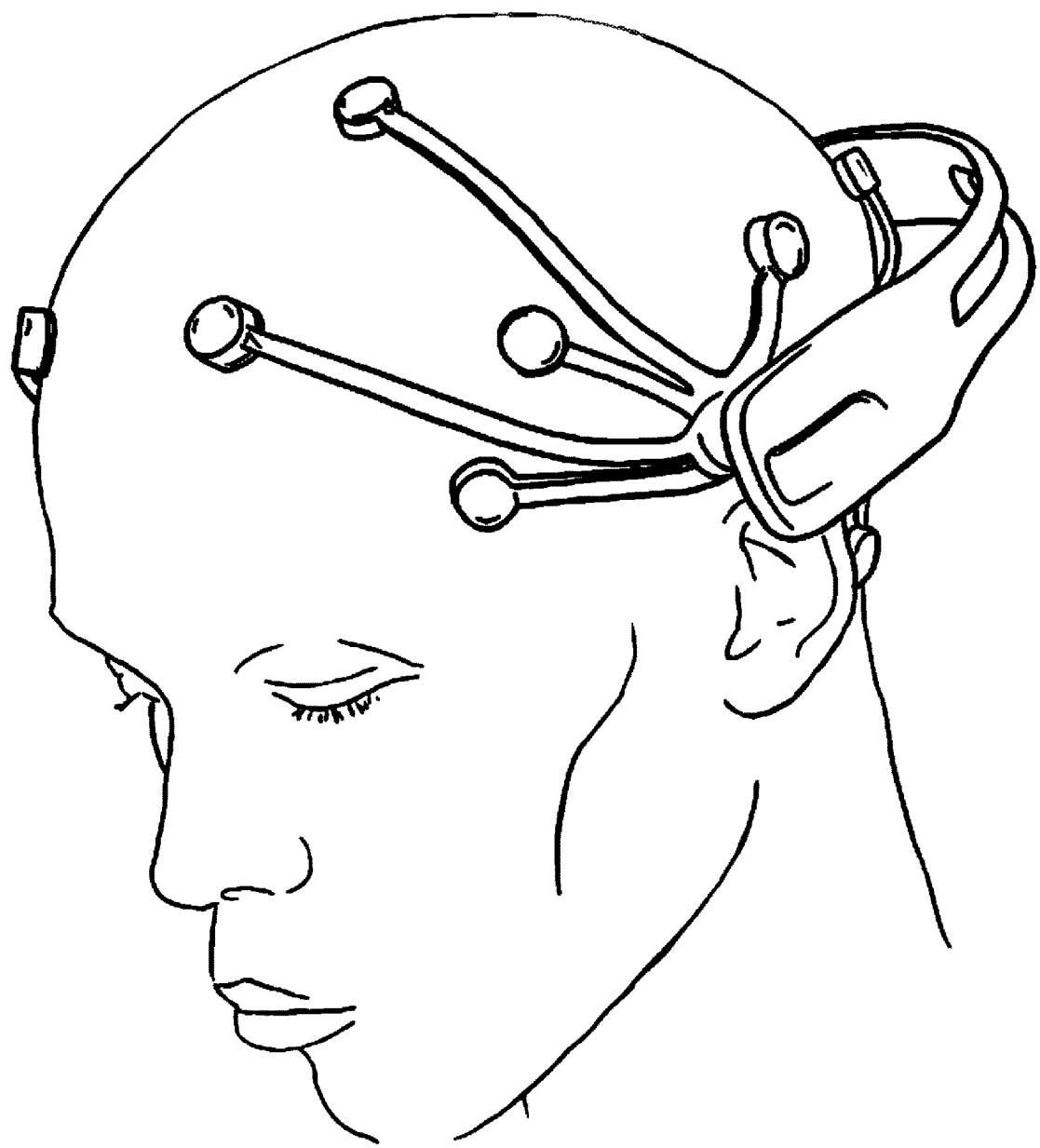
FIG. 4 shows a prior art Emotiv® headset design.
Figure 5A:
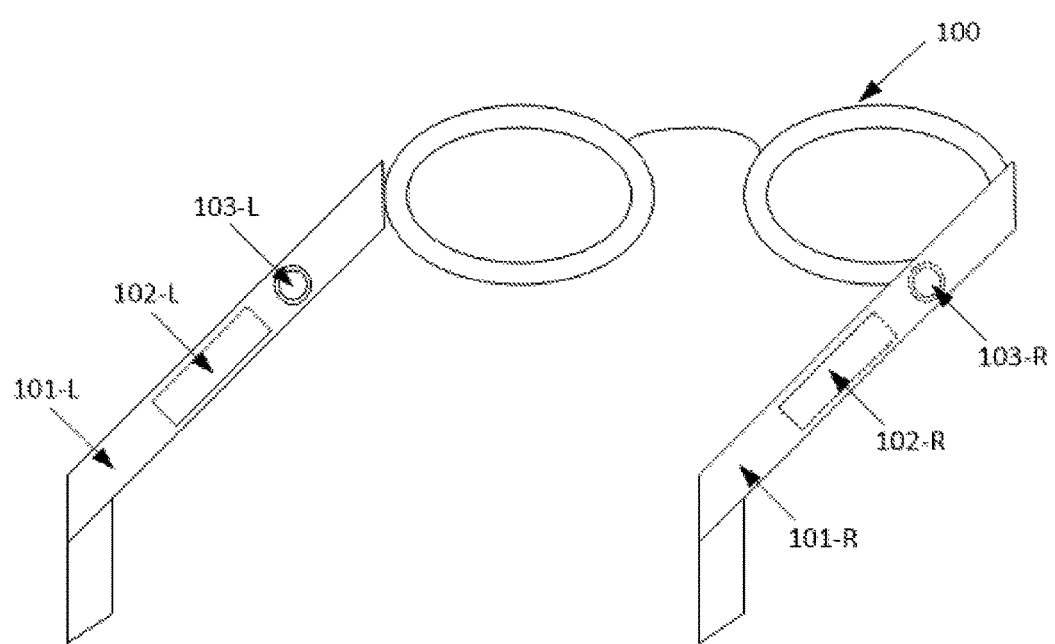
FIGS. 5A and 5B show respectively a perspective and top view of an eyeglass frame according to the present invention.
Figure 5B:
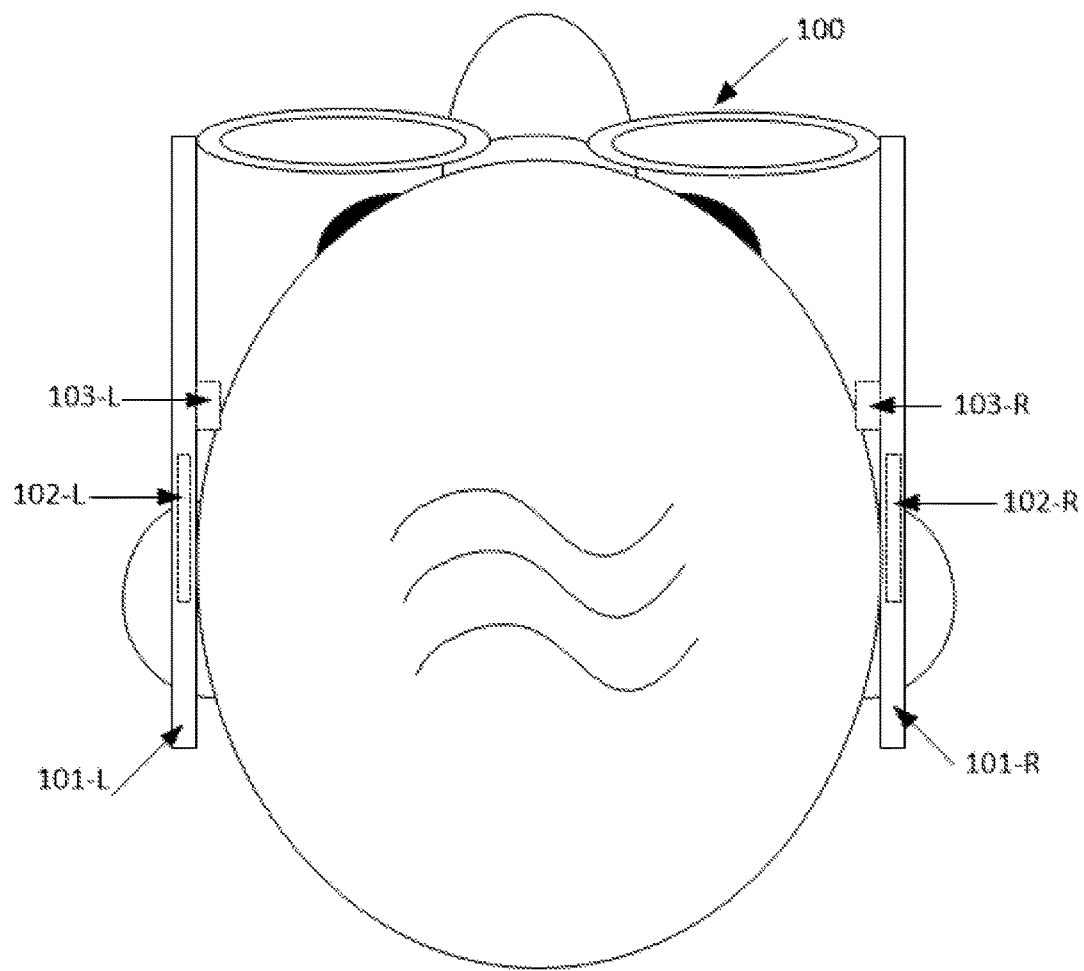

A system was developed based on an Android smartphone that was wirelessly connected to an Emotive headset (FIG. 4). In this design, an effective approach was implemented to recognize various eye movements and interpret them into control instructions on the mobile device. For instance, chains of eye movement patterns can automatically trigger an emergency call (e.g., three consecutive left and right saccades) or a pre-recorded text message (e.g., jaw clenching for 64 consecutive samples, determined by an EMG signal pattern), with the GPS location (FIG. 7). It is worthy to mention that, in order to achieve a true "hands-free" operation, all functions above were designed to launch using certain head and eye movement patterns, without finger actions.

EOG signals suffer from the presence of various artifacts or noise, which can be caused, for example, by the measurement circuitry and electrodes, or involuntary muscle movements and electrical activities along the scalp. However, they can be processed to remove artifacts that might hamper eye movement analysis. The processing can take a variety of forms and sequences. One source of interference is externally generated electromagnetic interference (EMI). Typically, the electrodes of the system are close together with respect to the source of the EMI, and therefore the EMI can be rejected as common mode interference. In other cases, external interference can come from local devices, such as the Google Glass device itself, which has an asymmetric topology and therefore emission pattern. Fortunately, the signals of interest in EOG are likely outside the EMI band of the Google Glass, and the interference would be expected to be AC coupled to the electrodes. The EMG signals from nearby muscles and electrocardiographic (ECG) signals may also be present in the electrode signals. While there can often be distinguished by frequency filtering, it may be useful to perform model-based filtering of the signal pattern (e.g., before filtering) to remove identifiable patterns. For example, ECG interference would typically follow an ECG pattern, and this can be intelligently filtered from the signal (or the signal intelligently analyzed to avoid interference from the ECG signal) without substantially degrading the remaining signal or its analysis. Similarly, EMG patterns may also be distinguished. In cases of intermittent strong interference (which in some cases can saturate signal processing components or algorithms), the system may detect the interference and stop processing until the interference ceases. For example, in an adaptive model, during the interference period, the adaptivity ceases, and therefore adaptation is limited to being based on valid signals only. By ceasing processing, rather than merely invalidating the output, recovery from the saturation or interference may be expedited.

Baseline drift is a slow signal change superposed on the EOG signal, and is caused by factors mostly unrelated to eye movements. Little study has been devoted to EOG signals with nonrepetitive characteristics. An approach based on wavelet transforms [10] may be used. The algorithm first performs an approximated multilevel 1D wavelet decomposition at level nine using Daubechies wavelets on each EOG signal component. The reconstructed decomposition coefficients give a baseline drift estimation. Subtracting this estimation from each original signal component yields the corrected signals with reduced drift offset. Of course, other baseline drift detection and correction systems and algorithms may be employed.

The nonrepetitive nature of EOG signals prohibits the application of denoising algorithms that make use of structural and temporal knowledge about the signal. However, a median filter may be employed, because it can preserve edge steepness of saccadic eye movements, retain EOG signal amplitudes, and not introduce any artificial signal changes. A critical requirement for the median filter is to choose a window size "Wmf" that is small enough to retain short signal pulses (particularly those caused by blinks), since it removes pulses of a width smaller than about half of its window size.

A variety of eye movements can be detected from EOG signals. The accuracy and robustness of the algorithms for detecting these eye movements is key to achieving good performance of the human-computer interface (HCI) infrastructure. Among all movement types, saccades (i.e., simultaneous movement of both eyes) are particularly important because the reliable eye movement encoding is highly reliant on it.

For saccade detection, a Continuous Wavelet Transform (CWT) algorithm may be employed, operating on inputs representing the denoised and baseline drift removed EOG signals. CWT first computes the continuous 1D wavelet coefficients at scale 20 using a Haar mother wavelet. Let s be one of these signal components and $\psi(t)$ the mother wavelet. The wavelet coefficient $C_b^a$ of s at scale a and position b is defined $$C_b^a(s) = \int_R \frac{1}{\sqrt{a}} \psi\left(\frac{t-b}{a}\right) dt$$

By applying an application-specific threshold $th_{sd}$ on the coefficients $C_i(s)=C_i^{20}(s)$, CWT creates a vector M with elements $M_i$:

$$M_i = \begin{cases} 1, & \forall_i : C_i(s) < -th_{sd} \\ -1, & \forall_i : C_i(s) > th_{sd} \\ 0, & \forall_i : -th_{sd} \leq C_i(s) \leq th_{ed} \end{cases}$$

This step divides EOG in saccadic (M=1,−1) and fixational (M=0) segments. Saccadic segments shorter than 20 ms and longer than 200 ms will be removed, according to the typical physiological saccade characteristics [5]. Given this CWT process, the saccade amplitude SA will be the difference in EOG signal amplitude before and after the saccade, and the saccade direction will be derived from the sign of the corresponding elements in M.

A particular activity may require saccadic eye movements of different distances and directions. Saccades are detected with two different amplitudes, "small" and "large." This requires two thresholds, $th_{sd}$ and $th_{sl}$, to divide the range of possible values of C into three bands:

no saccade ($-th_{sdsmall}<C<th_{sdsmall}$), small saccade ($-ths_{dlarge}<C<-th_{sdsmall}$ or $th_{sdsmall}<C<th_{sdlarge}$), and large saccade ($C<-th_{sdlarge}$ or $C>th_{sdlarge}$).

Figure 6A:
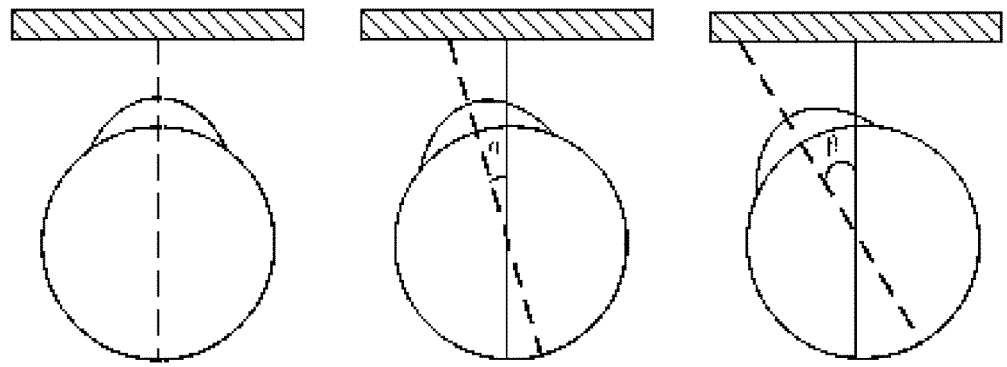
FIG. 6A shows graphically eye movement directions and amplitudes.

An "Eye Movement Encoded Human-Computer Interaction Language" is provided. Eye movements contain resourceful information that could be mapped to controlling instructions in HCI systems. For instance, activities such as reading typically involve characteristic sequences of several consecutive eye movements. However, the limited recognition accuracy and resolution in conventional vision-based eye movement trackers make them less effective in distinguishing finer changes of eye movement amplitude, as shown in FIG. 6A.

Figure 6B:
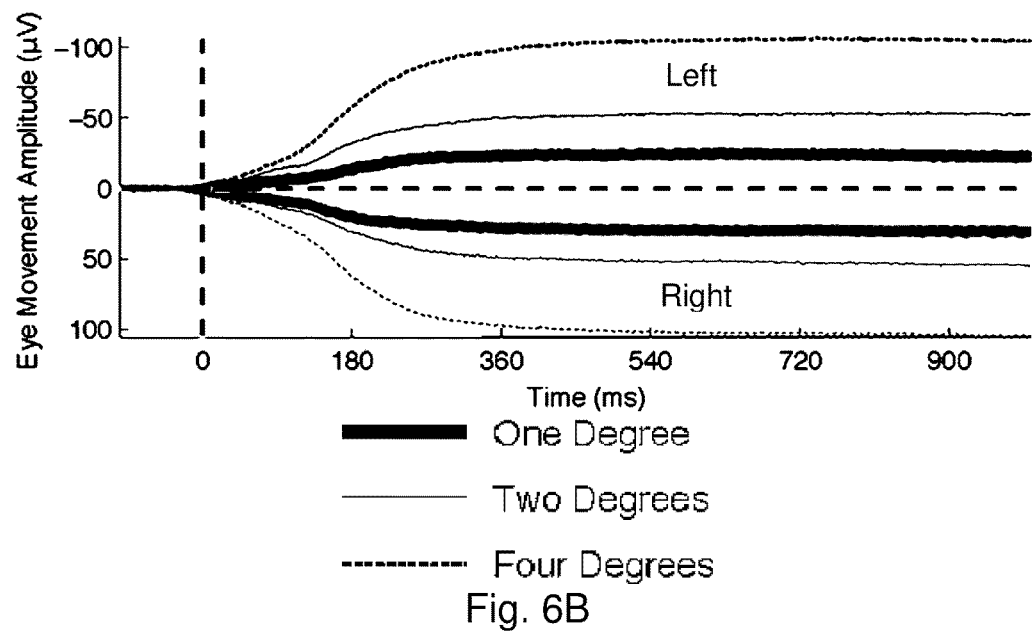
FIG. 6B shows eye movement angles reflected in EOG signals.
Figure 6C:
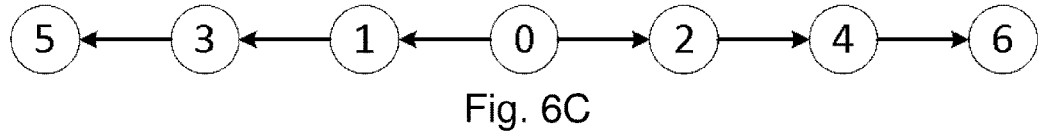
FIG. 6C shows a representative diagram of radix-7 encoding for eye movements.

According to the present technology, the EOG signals can be continuously and accurately measured by the embedded electrodes inside the glass arms, which enables the possibility of detecting finer eye movements. Thus, eye movements are encoded by mapping saccades with different amplitude to a discrete, number-based representation, as shown in FIG. 6B. Strings of these numbers are then collected in wordbooks that are analyzed to extract sequence information on repetitive eye movement patterns. Specifically, the algorithm takes the CWT saccades as its inputs and denotes the eye movements using the predefined encoding scheme. For example, assuming we can precisely distinguish three amplitude levels of eye movements in one direction, a radix-7 encoding scheme is defined, as shown in FIG. 6C, where "0" represents the look-straight-ahead state, and three different amplitudes of left and right gaze direction are further distinguished. Based on the encoded eye movements, a wordbook analysis assesses repetitive eye movement patterns that is defined as a string of successive numbers.

As an example with n=4, the pattern "large right→median left→small left→large left" translates to "6315."

It is noted that the sequence itself need not be detected in discrete steps. Rather, the available valid sequences may be designed for maximum separation, and to include what is effect an error correction code. Therefore, even if discrimination of the states of the EOG sequence is difficult or erroneous, the sequence of states may nevertheless be validly extracted. For example, because of baseline instability, relative changes in EOG state may be more accurately determined than absolute states. As a result, the sequence of EOG signal changes may be analyzed as a whole, without definitive determining the intermediate states. For example, the sequence "large right→median left→small left→large left" may be offset and appear to be "median right→large left→null→large left", which translates to "4505." However, if this is an invalid command, the system can then search for valid commands that have the same or similar transitions, which in this case the original sequences with left as "+", and right as "−"+3, −5, +3, −4, and the sequence as received is +2, −5, +3, −3. Therefore, by ensuring that the codespace is sparsely populated, and is absent ambiguity with respect to both absolute values and relative change values with respect to an error threshold, a high reliability may be obtained. Further, by combining EOG and EMG signal features (e.g., eyelid clenching), a relatively feature space may be developed.

Figure 1:
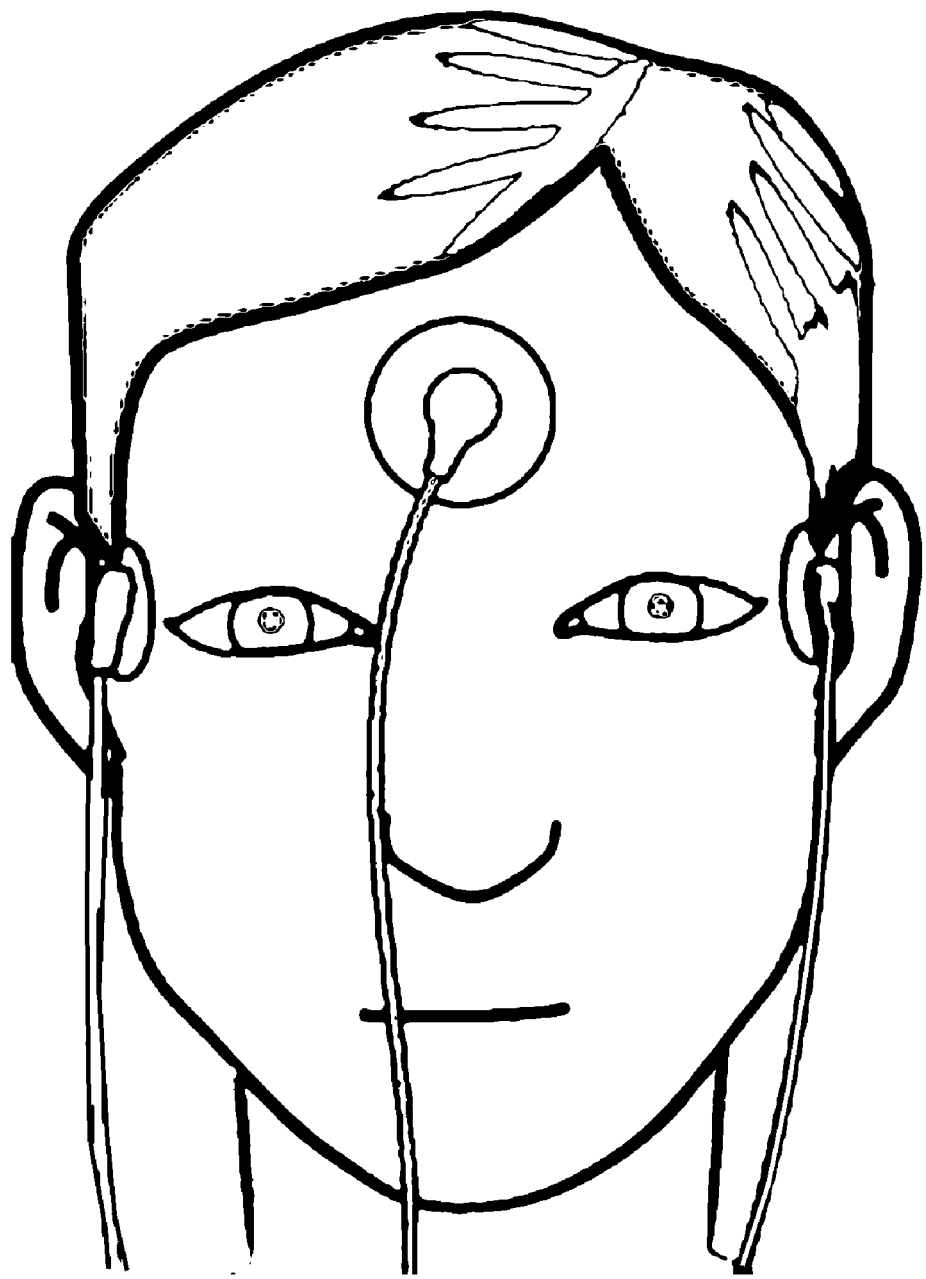
FIGS. 1 and 2 shows a prior art techniques for measuring EOG signals using self-stick electrodes.
Figure 2:
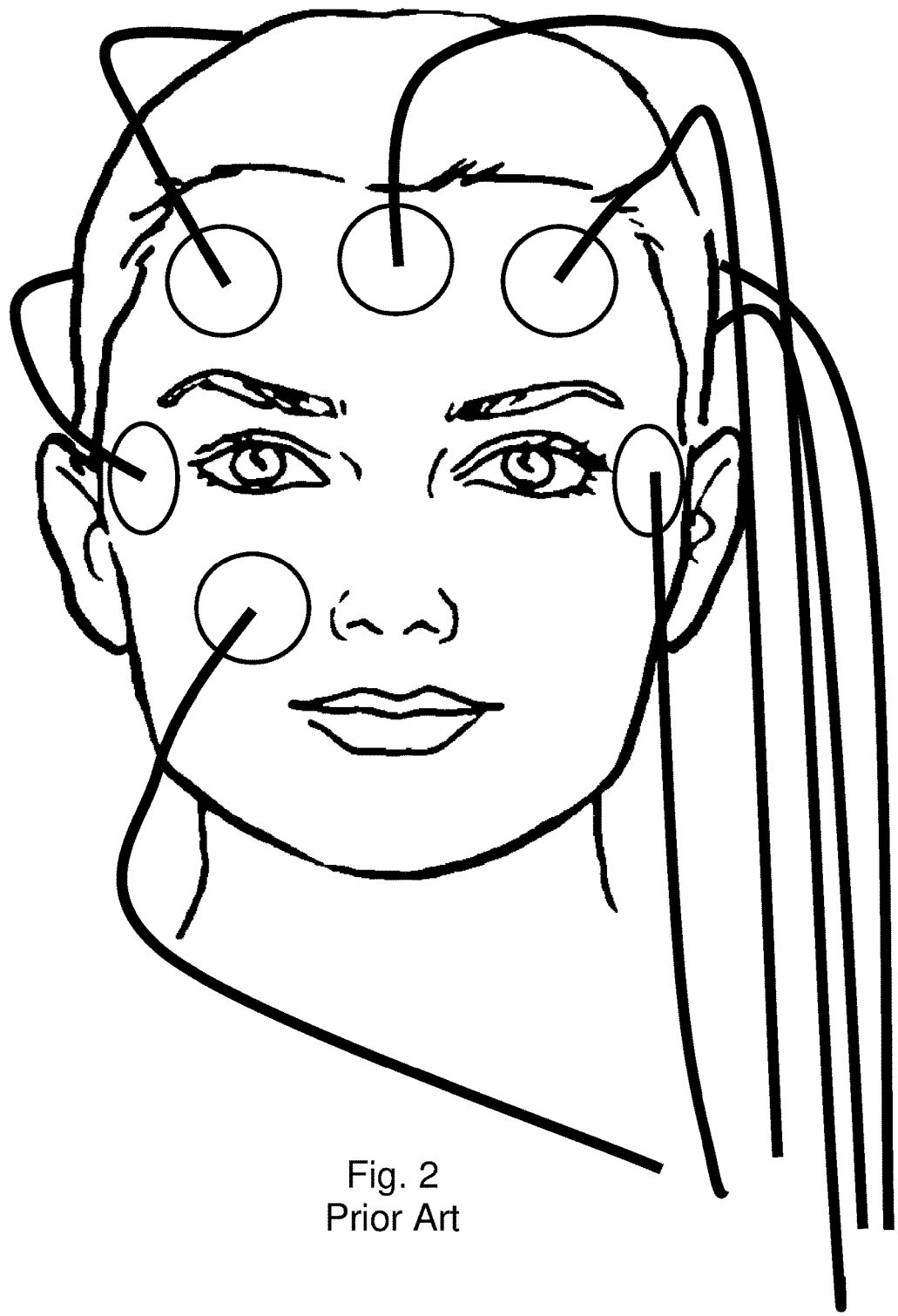
Figure 3:
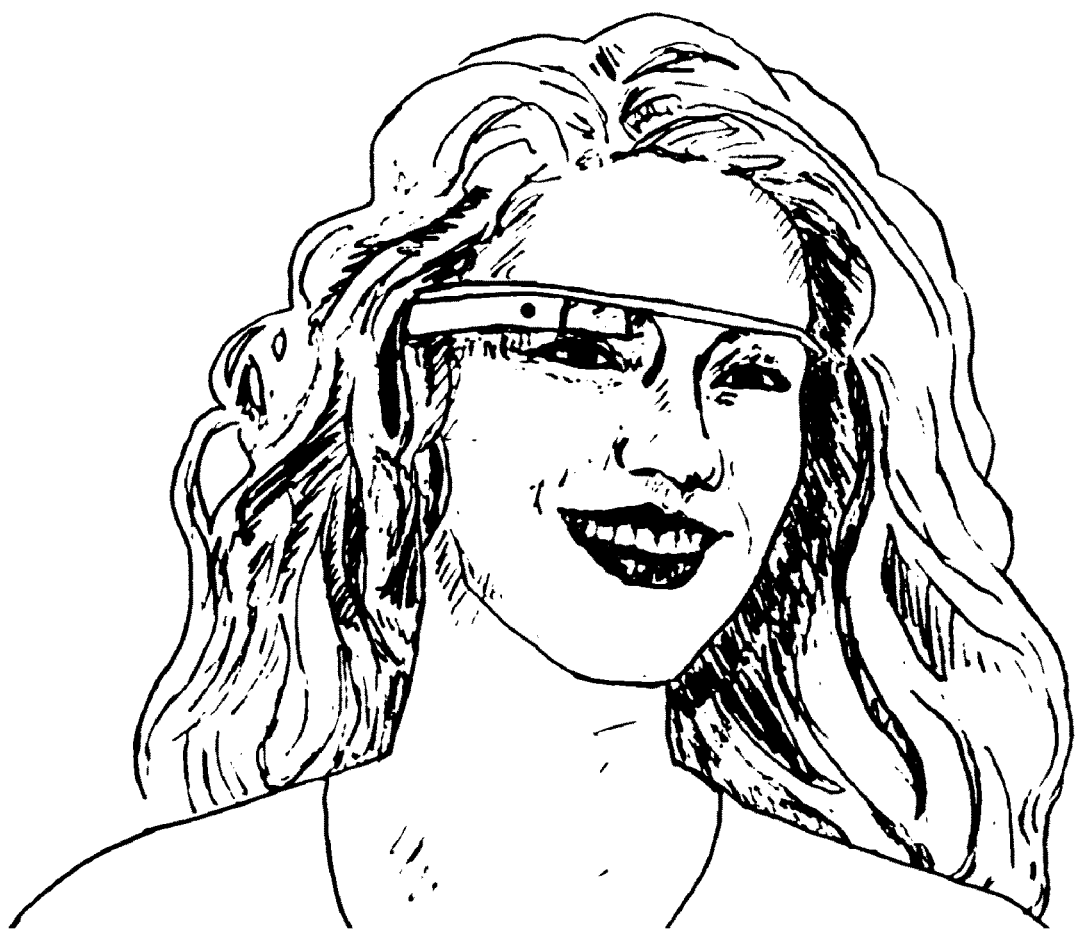
FIG. 3 shows a prior art Google Glass® frame design.
Figure 7A:
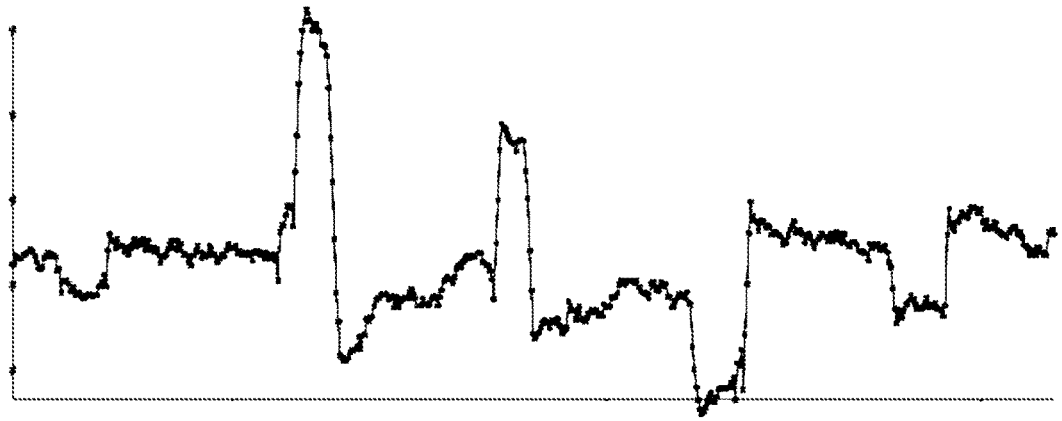
FIG. 7A shows a graph of EOG signals on a mobile phone display.
Figure 7B:
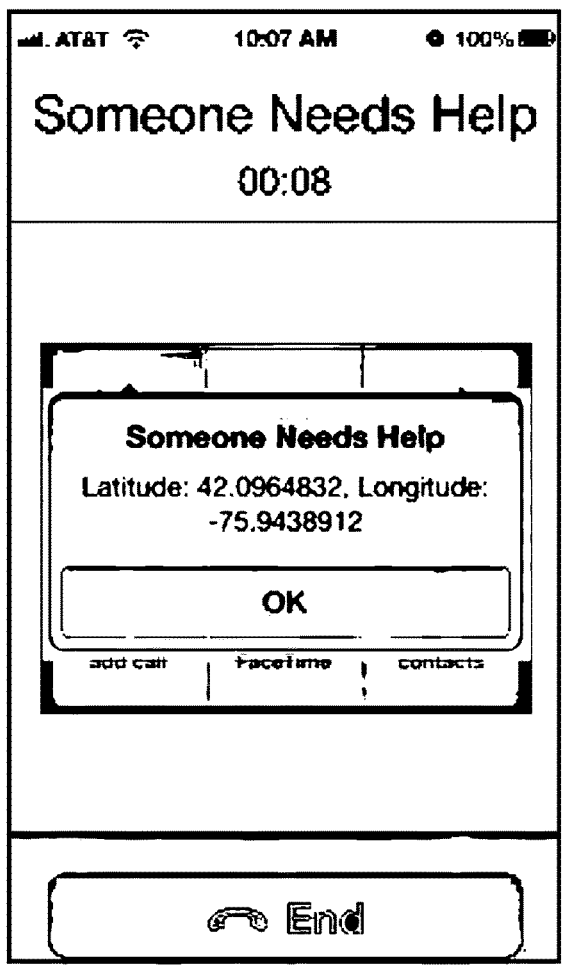
FIG. 7B shows an exemplary display on a mobile phone in which eye movements trigger a distress phone call with accompanying location information.

A prototype was developed [6] based on a Google Nexus smartphone that was wirelessly connected to an Emotive neuroheadset, shown in FIG. 3. In this prototype, the smartphone can receive and display real-time EOG data, as shown in FIG. 7A. An effective approach was implemented to recognize various eye movements (e.g., left/right saccades) and interpret them into control instructions on the mobile device. Along with the built-in accelerometer, the prototype can achieve precise control of a moving cursor on the phone screen, just like a mouse. Furthermore, chains of eye movement patterns can automatically trigger an emergency call (three consecutive left and right saccades) or a pre-recorded text message (jaw clenching for 64 consecutive samples), with the GPS location, as shown in FIG. 7B. It is worthy to mention that, in order to achieve a true "hands-free" operation, all above three apps were designed to launch and switch using certain head and eye movement patterns, without body actions.

The eye movements can also be representative of gestures, such as sweeps,

The system computer system may be implemented according to designs disclosed in, for example, US Patent Application and Patent Nos. 20140316235; 20140313303; 20140304122; 20140303994; 20140295786; 20140286566; 20140285634; 20140276239; 20140272894; 20140272847; 20140266604; 20140258110; 20140257047; 20140251233; 20140244514; 20140244495; 20140244494; 20140204229; 20140204190; 20140164111; 20140161412; 20140133658; 20140108151; 20140052555; 20140044304; 20140040041; 20140039571; 20140029809; 20130325493; 20130311329; 20130223673; 20130093829; U.S. Pat. Nos. 8,878,749; 8,874,760; 8,867,139; 8,867,131; 8,866,702; 8,862,764; 8,860,787; 8,856,948; 8,854,282; 8,838,708; 8,833,934; 8,831,879; 8,827,445; 8,823,740; 8,820,934; 8,817,379; 8,812,419; 8,811,951; 8,798,336; 8,786,953; 8,775,844; 8,773,599; 8,767,306; 8,767,305; 8,764,185; 8,762,895; 8,760,765; 8,750,541; 8,749,886; 8,738,723; 8,738,292; 8,724,206; 8,705,177; 8,686,924; 8,676,893; 8,670,000; 8,665,178; 8,661,053; 8,659,433; 8,629,815; 8,612,211; 8,611,015; 8,593,795; 8,558,759; 8,542,879; 8,510,166; 8,508,851; 8,506,080; 8,505,090; 8,457,367; 8,411,909; 8,384,617; 8,332,424; 8,319,746; 8,316,319; 8,311,289; 8,303,110; 8,294,994; 8,275,893; 8,235,529; 8,228,315; 8,223,088; 8,223,024; 8,217,856; 8,209,183; 8,203,502; 8,199,126; 8,194,036; 8,190,749; 8,184,070; 8,184,067; 8,179,604; 8,176,437; 8,175,297; and 8,146,156.

A typical system will provide a quad core ARM architecture processor with GPU, random access memory, flash memory, WiFi and Bluetooth connectivity, optionally 3G, 4G and/or LTE connectivity, an LCD, OLED, and/or heads-up display projecting an image to the eye within the eyeglass frames, a sensor package including still/video cameras, microphone, accelerometer, magnetometer, gyroscope, touchpad, fingerprint scanner, hand-gesture sensor, a rechargeable lithium ion battery, speaker(s), and other standard elements.

The EOG electronics typically employ instrumentation amplifiers configured to provide a high differential gain with high common mode rejection ratio, and preferably a digitally controllable gain. The amplified signal(s) are digitized, and most complex signal processing performed by a standard processor or digital signal processor.

The system may be provided as an operating system resource, to provide input for all applications, or through each application individually. In order to provide context-independent functionality, such as emergency calling, operating system level services are preferred.

The above description of the invention is intended to be illustrative and not limiting. Various changes or modifications in the embodiments described may occur to those skilled in the art. These can be made without departing from the spirit or scope of the invention.

What is claimed is:

1. An apparatus for detecting electrooculograph (EOG) signals, comprising:
a pair of temple pieces connected to a bridging structure;
at least one electrode on each temple piece configured to contact the skin at the temple, and to receive an EOG signal from a proximate orbital socket;
a reference electrode displaced from each temple; and
a processor configured:
to process signals from the at least one electrode on each temple piece and the reference electrode to detect saccade movements of the eyes; and
characterize a sequence of states of the received EOG signal as a single user command selected from a wordbook of valid user commands.

2. The apparatus according to claim 1, wherein the at least one electrode on each temple piece configured to contact the skin at the temple comprises at least two electrodes, configured to determine changes in a vertical and horizontal axis of the EOG signal.

3. The apparatus according to claim 1, wherein the processor is further configured to perform baseline drift compensation by performing a wavelet transform decomposition of the EOG signal to provide wavelet transform coefficients, estimate a baseline drift based on the wavelet transform coefficients, and to compensate the baseline drift based on the estimated baseline drift.

4. The apparatus according to claim 1, wherein the processor is further configured to:
perform an approximated multilevel 1D wavelet decomposition at level nine using Daubechies wavelets on each EOG signal to produce a set of decomposition coefficients;
estimating a drift of the EOG baseline using the decomposition coefficients; and
subtracting the estimated drift of the EOG baseline from each EOG signal.

5. The apparatus according to claim 1, wherein the processor is further configured to implement median filter denoising, having a window sufficiently small to retain short signal pulses associated with eye blinks.

6. The apparatus according to claim 1, wherein the processor is configured to separately analyze movement of right and left eyes separately.

7. The apparatus according to claim 6, wherein the processor is configured to determine consistency of right and left eye saccadic movements.

8. The apparatus according to claim 1, wherein the processor is further configured to:
perform a continuous wavelet transform (CWT) on the EOG signals;
applying a threshold on the coefficients of the CWT transform to segment the EOG signal into periods of saccadic movement and fixation;
filtering saccadic periods based on duration; and
determining a signed saccade amplitude for each filtered period.

9. The apparatus according to claim 1, wherein the processor is further configured to:
perform a Continuous Wavelet Transform (CWT) on the EOG signals s, wherein the CWT first computes continuous 1D wavelet coefficients using a Haar mother wavelet, wherein:
$\psi(t)$ is the mother wavelet;

$$C_b^a(s) = \int_R \frac{1}{\sqrt{a}} \psi\left(\frac{t-b}{a}\right) dt$$

are the wavelet coefficients $C_b^a$ of s at scale a and position b;
applying a threshold $th_{sd}$ on the coefficients $C_i(s)=C_i^{20}(s)$, to create a vector M with elements $M_i$:

$$M_i = \begin{cases} 1, & \forall_i : C_i(s) < -th_{sd} \\ -1, & \forall_i : C_i(s) > th_{sd} \\ 0, & \forall_i : -th_{sd} \leq C_i(s) \leq th_{ed} \end{cases}$$

to divide the EOG signal into periods of saccadic (M=1,−1) and fixational (M=0) segments;
removing saccadic segments shorter than 20 ms and longer than 200 ms; and
determining a saccade amplitude SA for each segment as a difference in EOG signal amplitude from a baseline EOG signal amplitude, and determining a saccade direction based on a sign of the corresponding elements in M.

10. The apparatus according to claim 1, wherein an amplitude of the EOG signal during a saccade movement is corrected for a change in baseline by subtracting an amplitude of the EOG signal during a time when a saccade is not detected temporally proximate to the saccade movement.

11. A method for detecting electrooculograph (EOG) signals, comprising:
providing a pair of temple pieces connected to a bridging structure to a human or animal, having at least one electrode on each temple piece configured to contact the skin at the temple, and to receive an EOG signal from a proximate orbital socket and a reference electrode displaced from each temple;
processing electronic signals from the at least one electrode on each temple piece to detect saccade movements of the eyes; and
characterizing a sequence of a plurality of amplitudes and signs of the EOG signal over a period of time as a single user command selected from a wordbook of valid user commands.

12. The method according to claim 11, wherein said processing comprises determining a baseline EOG signal amplitude during an absence of saccade movements, and determining an amplitude and a sign of the EOG signal during a saccade movement.

13. The method according to claim 11, wherein the at least one electrode on each temple piece configured to contact the skin at the temple comprises a plurality of electrodes on each temple piece, configured to determine changes in a vertical and horizontal axis of the EOG signal.

14. The method according to claim 11, further comprising:
compensating for a drift of a baseline of the EOG using decomposition coefficients of a wavelet decomposition on each EOG signal; and
implementing a median filter to denoise the baseline drift compensated EOG signal, having a window sufficiently small to retain short signal pulses associated with eye blinks.

15. The method according to claim 14, further comprising:

determining, based on coefficients of a continuous wavelet transform of the EOG signals, respective periods of eye saccadic movement and eye fixation;

filtering the periods of eye saccadic movement based on duration to eliminate periods of eye saccadic movement below and above respective lower and upper thresholds; and determining a signed saccade amplitude for each filtered period.

16. A method for detecting electrooculograph (EOG) signals from eyes of a human or animal, comprising:

providing a pair of temple pieces connected to a bridging structure supported by a nose of the human or animal, having at least one electrode on each temple piece configured to contact the skin at the temple, substantially without contacting an infraorbital facial surface, and to receive an EOG signal from a proximate orbital socket and a reference electrode displaced from each temple;

processing electronic signals from the at least one electrode on each temple piece and the reference electrode to characterize an amplitude and direction of saccadic movements of the eyes and fixation of the eyes; and interpreting sequences comprising a plurality of characterized amplitudes and directions of saccadic movements of the eyes and fixations of the eyes over a period of time as a single user command selected from a wordbook of valid user commands.

17. The method according to claim 16, further comprising processing electronic signals from the at least one electrode on each temple piece and the reference electrode to characterize electromyographic signals.

18. The method according to claim 16, wherein the at least one electrode on each temple piece configured to contact the skin at the temple comprises a plurality of electrodes on each temple piece, configured to determine changes in a vertical and horizontal axis of the EOG signal.

19. The method according to claim 16, further comprising:

compensating for a drift of a baseline of the EOG signals using decomposition coefficients of a wavelet decomposition on each EOG signal; and implementing a median filter to denoise the baseline drift compensated EOG signal, having a window sufficiently small to retain short signal pulses associated with eye blinks.

20. The method according to claim 19, further comprising:

determining, based on coefficients of a continuous wavelet transform of the EOG signals, respective periods of eye saccadic movement and eye fixation;

filtering the periods of eye saccadic movement based on duration to eliminate periods of eye saccadic movement below and above respective lower and upper thresholds; and determining a signed saccade amplitude for each filtered period.

* * * * *